США009108011B2

(12) United States Patent
Wachtel et al.

(10) Patent No.: US 9,108,011 B2
(45) Date of Patent: Aug. 18, 2015

(54) INHALATION DEVICE

(75) Inventors: Herbert Wachtel, Ingelheim am Rhein (DE); Deborah Bickmann, Urbar (DE); Sarina Linz, Urbar (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 857 days.

(21) Appl. No.: 13/266,137

(22) PCT Filed: Apr. 15, 2010

(86) PCT No.: PCT/EP2010/002315
§ 371 (c)(1),
(2), (4) Date: Jan. 24, 2012

(87) PCT Pub. No.: WO2010/124795
PCT Pub. Date: Nov. 4, 2010

(65) Prior Publication Data
US 2013/0025594 A1    Jan. 31, 2013

(30) Foreign Application Priority Data
Apr. 28, 2009  (EP) .................................... 09005863

(51) Int. Cl.
*A61M 15/00* (2006.01)

(52) U.S. Cl.
CPC ......... *A61M 15/0086* (2013.01); *A61M 15/009* (2013.01); *A61M 15/0088* (2014.02); *A61M 2202/0468* (2013.01)

(58) Field of Classification Search
CPC ..................... A61M 15/0086; A61M 15/0088; A61M 15/00; A61M 15/0016; A61M 16/08; A61M 15/0018; A61M 15/0015; A61M 15/0028; A61M 11/003; A61M 15/0026; A61M 15/004; A61M 15/009; A61M 11/00; A61M 16/20; A61M 11/007; A61M 16/06; A61M 16/00; A61M 5/08; A61M 5/091; A61M 15/0043; A61M 15/0023; B02B 15/00; B02B 15/068; A61B 5/091; A61B 5/08; B65D 83/30
USPC ............. 128/200.11–200.24, 203.12, 203.15, 128/205.13–205.17, 203.21, 203.23, 128/203.24, 203.28, 203.29
See application file for complete search history.

(56) References Cited

U.S. PATENT DOCUMENTS 3,923,043 A * 12/1975 Yanda ........................... 600/541
4,498,472 A *  2/1985 Tanaka ..................... 128/203.28

(Continued)

FOREIGN PATENT DOCUMENTS

CA    2297174 A1    2/1999
DE    3513628 C1   10/1986

(Continued)

OTHER PUBLICATIONS

International Search Report for PCT/EP2010/002315 mailed Sep. 3, 2010.

*Primary Examiner* — Annette Dixon
(74) *Attorney, Agent, or Firm* — Michael P. Morris; Mary-Ellen M. Devlin

(57) ABSTRACT

The invention relates to an inhalation device (FIG. 1) having a connection device (4) and a container (8) connected or connectable thereto and collapsing upon inhaling, for intermediately storing an aerosol. In order to increase the fine particle count of the dispensed aerosol, the container (8) at least substantially retains the length thereof when collapsing, and/or tapers down toward the free end thereof.

17 Claims, 6 Drawing Sheets

(56) References Cited

U.S. PATENT DOCUMENTS

| | | | | |
|---|---|---|---|---|
| 5,020,530 | A | * | 6/1991 | Miller .................. 128/203.28 |
| 5,099,833 | A | * | 3/1992 | Michaels ............... 128/200.14 |
| 5,613,489 | A | * | 3/1997 | Miller et al. ........... 128/203.28 |
| 5,833,088 | A | | 11/1998 | Kladders et al. |
| 6,390,090 | B1 | * | 5/2002 | Piper .................... 128/203.28 |
| 6,401,710 | B1 | | 6/2002 | Scheuch et al. |
| 6,571,791 | B2 | | 6/2003 | Scheuch et al. |
| 7,802,568 | B2 | | 9/2010 | Eicher et al. |
| 8,413,651 | B2 | * | 4/2013 | Powell et al. ........... 128/203.12 |
| 2003/0064032 | A1 | | 4/2003 | Lamche et al. |
| 2006/0000471 | A1 | | 1/2006 | Klein |
| 2008/0029099 | A1 | | 2/2008 | Storz |
| 2010/0163045 | A1 | * | 7/2010 | Powell et al. ........... 128/203.29 |

FOREIGN PATENT DOCUMENTS

| | | |
|---|---|---|
| DE | 20018588 U1 | 1/2001 |
| EP | 0965355 A2 | 12/1999 |
| EP | 1003478 A1 | 5/2000 |
| EP | 1163921 A1 | 12/2001 |
| EP | 1884254 A1 | 2/2008 |
| WO | 9114468 A1 | 10/1991 |
| WO | 9606011 A2 | 2/1996 |
| WO | 9712687 A1 | 4/1997 |
| WO | 0049988 A2 | 8/2000 |
| WO | 2003068299 A1 | 8/2003 |
| WO | 2008124666 A2 | 10/2008 |

* cited by examiner

INHALATION DEVICE

FIELD OF THE INVENTION

The present invention relates to an inhalation device for the intermediate storage of an aerosol, having a connecting device and a container that is connected or connectable thereto and that collapses during inhalation.

BACKGROUND OF THE INVENTION

A problem with inhalers or nebulisers in general is that the triggering of the nebulisation of a medicament preparation and the breathing in has to be coordinated. This may be difficult for the individual user. In particular, it has been found that such co-ordination is difficult precisely for children. Studies have shown that the aerosol produced is often not optimally inhaled by unskilled users or children, for example.

EP 1163921 B1 discloses an inhalation device for intermediately storing a nebulised medicament preparation (an aerosol) in a container that collapses during inhalation. The known inhalation device comprises a preferably transparent housing in which the container is arranged. The container is preferably configured as a substantially elongate or cylindrical bellows which collapses in the axial or longitudinal direction during inhalation. The known inhalation device comprises a control device for keeping the inhalation flow substantially constant throughout the entire inhalation of the aerosol. Experiments have shown that the fine particle count of the known inhalation device is not optimal.

SUMMARY OF THE INVENTION

The present invention is based on the problem of providing an inhalation device for intermediately storing a nebulised medicament preparation or an aerosol, wherein the inhalation device makes it possible to have a higher fine particle count than in the prior art and/or is very simple or inexpensive in its construction.

The above problem is solved by an inhalation device for the intermediate storage of an aerosol, having a connecting device and a container that is connected or connectable thereto and that collapses during inhalation. Advantageous further features are described herein.

The present invention relates in particular to an inhalation device for so-called soft mist inhalation in which a spray mist (aerosol) is produced that spreads out only relatively slowly. Spray mists of this kind as described in the present invention are delivered in particular at a speed of less than 2 m/s, preferably less than 1.5 m/s and most particularly preferably less than 1 m/s (measured in each case at a distance of 10 cm from a discharge nozzle).

During the inhalation of a nebulised medicament preparation or aerosol it is essential or desirable to achieve the highest possible proportion of fine particles since essentially only these particles reach the desired regions of the lungs during inhalation. The term "fine particle count" in the present invention denotes the proportion of particles that have an aerodynamic diameter of 5 μm or less, based on the total quantity delivered.

In a first aspect of the present invention, the container that collapses during inhalation is configured so that as it collapses it retains its length at least substantially. As a result, the container is able to collapse more easily and/or more favourable flow conditions can be achieved in the container during the inhalation or collapsing and/or during the filling of the container with a nebulised medicament preparation or aerosol. This contributes to a higher fine particle count during inhalation.

In a second aspect of the present invention the container tapers towards a free end. In particular, the container is connected or connectable to a connecting device of the inhalation device at one end and is at least substantially flat at the other (free) end. As a result, the container is able to collapse more easily and/or more favourable flow conditions can be achieved in the container during the inhalation or collapsing and/or during the filling of the container with a nebulised medicament preparation or aerosol. This contributes to a higher fine particle count during inhalation.

In a third aspect of the present invention the container is preferably constructed so as not to be self-expanding. As a result, the container is able to collapse more easily and/or more favourable flow conditions can be achieved in the container during inhalation or collapsing and/or during the filling of the container with a nebulised medicament preparation or aerosol. This contributes to a higher fine particle count during inhalation.

In a fourth aspect of the present invention the container has its maximum diameter or cross-section at its removal end, and in particular increases in diameter or cross-section towards its removal end. As a result, the container is able to collapse more easily and/or more favourable flow conditions can be achieved in the container during inhalation or collapsing and/or during the filling of the container with a nebulised medicament preparation or aerosol. This contributes to a higher fine particle count during inhalation.

In a fifth aspect of the present invention the inhalation device is constructed solely from a connecting device that widens out preferably in a funnel shape and a bag that is connected or connectable thereto as a container; thus, in particular, no housing or the like is provided. The connecting device then forms a mouthpiece and also a holder for the container. As a result, the container is able to collapse more easily and/or more favourable flow conditions can be achieved in the container during inhalation or collapsing and/or during the filling of the container with a nebulised medicament preparation or aerosol. This contributes to a higher fine particle count during inhalation.

In a sixth aspect of the present invention the inhalation device comprises a connecting region for the container that widens out in a funnel shape, particularly with a diameter such that standard commercial bags, sandwich bags or the like can be connected thereto as the container. As a result, the container is able to collapse more easily and/or more favourable flow conditions can be achieved in the container during inhalation or collapsing and/or during filling of the container with a nebulised medicament preparation or aerosol. This contributes to a higher fine particle count during inhalation.

The above-mentioned aspects of the present invention and/or aspects and features of the present invention explained hereinafter may be achieved independently of one another and in any desired combination.

The proposed solution allows a more defined inhalation of the active substance, with an on average higher and/or less fluctuating content of active substance deposited in the lungs. This allows improved treatment of children and/or a broadening of the indication or use of other medicament preparations.

BRIEF DESCRIPTION OF THE DRAWINGS

Further features, advantages, properties and aspects of the present invention will become apparent from the claims and the following description of preferred embodiments by reference to the drawings, wherein.

In the figures, the same reference numerals are used for identical or similar parts, where corresponding or similar properties and advantages are achieved even if there is no repetition of the description.

DETAILED DESCRIPTION OF THE INVENTION

Figure 1:
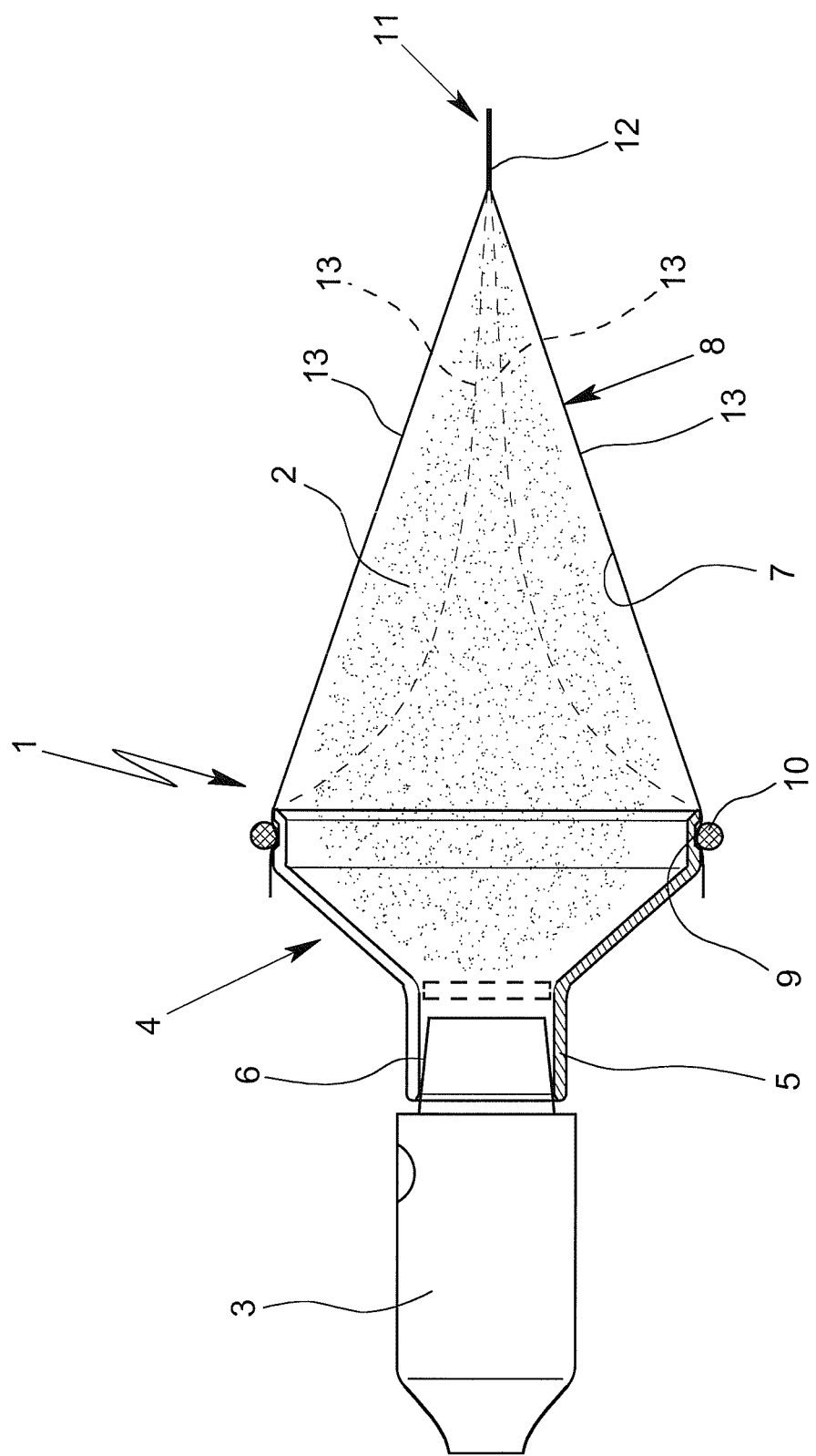
FIG. 1 shows a schematic sectional view of an inhalation device according to a first embodiment with an associated inhaler.

FIG. 1 shows in a schematic sectional view an inhalation device 1 according to a first embodiment of the present invention. The inhalation device 1 serves for intermediately storing an aerosol 2. The aerosol 2 is, in particular, a nebulised medicament preparation which is to be inhaled.

The aerosol 2 is preferably produced or provided by an aerosol dispenser, in this case an inhaler 3, a nebuliser or the like, and delivered or metered into the inhalation device 1. Particularly preferably, the aerosol 2 is a medicament preparation or the like which is nebulised without the use of propellant gas. However, the aerosol 2 may also be produced by propellant gas-driven nebulisation or propellant gas-assisted nebulisation.

The inhalation device 1 is preferably temporarily connectable to the aerosol dispenser or inhaler 3 or the like fluidically and preferably also mechanically. FIG. 1 shows the inhalation device 1 in its state of attachment to the inhaler 3 and in its state of having already been filled with the aerosol 2.

The inhalation device 1 comprises a connecting device 4 for fluidically and preferably also mechanically connecting the inhalation device 1 to the inhaler 3 or other aerosol dispenser or nebuliser or the like, in the embodiment shown, for introducing or receiving the aerosol 2 and/or for dispensing the aerosol 2 which it has received or intermediately stored, particularly to a user or patient (not shown) during inhalation.

In the embodiment shown the connecting device 4 has a preferably tube-like attachment portion 5 for receiving and/or dispensing the fluid. The attachment portion 5 in the embodiment shown can preferably be pushed onto or inserted into a mouthpiece 6 of the inhaler 3. In particular, the inhalation device 1 or its connecting device 4 or the attachment portion 5 thereof can be releasably connected to the inhaler 3 by a clamping or latching action. However, other design solutions are also possible.

It should be noted that in the embodiment shown the connecting device 4 preferably has only one combined inlet and outlet for the aerosol 2, in this case in the form of the attachment portion 5. However, the inflow and outflow may also be constructed separately.

The attachment portion 5 is preferably of round or oval construction on the inside and/or outside.

The aerosol 2 is accommodated in a receiving chamber 7 of the inhalation device 1 for intermediate storage.

The inhalation device 1 comprises a container 8 for receiving or intermediately storing the aerosol 2 or for forming (at least the majority of) the receiving chamber 7.

The container 8 is preferably constructed such that it collapses during inhalation, i.e. when the aerosol 2 is removed from the inhalation device 1 or from the receiving chamber 7 or from the container 8.

The container 8 is preferably made from a flexible and/or soft and/or deformable material, particularly paper, film, a suitable composite material or the like.

The container 8 is preferably constructed as a bag.

The container 8 is fluidically and preferably also mechanically connected or connectable to the connecting device 4 or its attachment portion 5. In the embodiment shown, the container 8 is held by the connecting device 4. Preferably, the connecting device 4 comprises a connecting portion 9 for connecting to the container 8.

The container 8 is preferably connected or connectable to the connecting device 4 or connecting portion 9 in releasable, replaceable and/or clamping manner, most preferably in the embodiment shown by means of a ring or fixing means 10, such as a rubber band, O-ring, clamping ring or the like, which for example holds the container 8 in a clamping and/or positively locking manner on the preferably tube-like connecting portion 9 or an outer periphery of the connecting portion 9. However, other design solutions are also possible. For example, the container 8 may have a reinforced edge or connecting region which is connectable to the connecting device 4 or connecting portion 9 by a clamping action and/or in some other way.

The container 8 is preferably connected or connectable to the connecting device 4 or its connecting portion 9 at one end 11. At the other (free) end 11 the container 8 is closed off.

The container 8 is particularly preferably closed off by a sealing or weld seam 12 at its free end 11.

The container 8 is preferably of elongate construction. The container 8 is preferably configured such that as it collapses it at least substantially maintains its length.

The container 8 is preferably constructed to taper towards its free end 11.

The container 8 is of flat construction at least in part, particularly at its free end 11.

The container 8 has a diameter and/or cross-section that preferably increases from the free end 11 towards the connecting device 4.

The diameter or cross-section of the container 8 is preferably at its greatest in the region of the attachment to the connecting device 4 or the connecting portion 9.

The container 8 is preferably at least substantially wedge-shaped.

The container 8 preferably comprises two opposing flat sides 13 which move towards each other or collapse or are pulled together during inhalation, i.e. as the aerosol 2 is dispensed from the inhalation device 1, as the container 8 collapses.

FIG. 1 shows by dashed lines the container 8 in the collapsed state, i.e. after the removal of (a substantial part of) the aerosol 2. In particular, the flat sides 13 have collapsed. The flat sides 13 may also be curved and be inwardly convex, in particular. Moreover, the axial length or the length of the container 8 in the direction of inflow and outflow of the aerosol 2 may decrease to some extent. However, this is not regarded as a substantial change in the length of the container 8 in the present invention. Rather, this is taken to mean that the container 8 at least substantially retains its length as it collapses.

The collapsing of the container 8 takes place in particular only as a result of the aerosol 2 being sucked out of the receiving chamber 7. The container 8 should accordingly collapse as easily as possible in order that the aerosol 2 can be removed with the smallest possible loss of pressure.

The proposed container 8 collapses particularly easily, thanks to its shape. This assists with the dispensing of the aerosol 2 with a particularly high fine particle count.

Because of the wedge-shaped form or because of the diameter and/or cross-section of the container 8 decreasing preferably continuously towards the free end 11, the average distance that the aerosol 2 has to travel as a whole as it is received and dispensed must be less than in a container 8 having a cross-section that is substantially constant over its entire length.

The container 8 may have a substantially rectangular or round, particularly oval or circular cross-section in the region of its connection to the connecting device 4. However, other shapes are also possible.

It should be pointed out that the container 8 may also be connected to the connecting device 4 via a flexible connecting region 9, the connecting opening of which, towards the container 8, may optionally itself be capable of collapsing.

After the inhalation device 1 or the container 8 has received the aerosol 2 for intermediate storage, the aerosol dispenser or the inhaler 3 or the like is separated from the inhalation device 1. Then a user or patient (not shown) is able to remove the aerosol 2 from the inhalation device 1 by breathing in or inhaling. For this purpose the inhalation device 1 or connecting device 4 has a corresponding removal option. This removal option is particularly preferably provided by the attachment portion 5 which is for this purpose connectable to a mouthpiece or the like (not shown), for example, and/or itself forms a mouthpiece for the user or patient. Particularly preferably, the user or patient is thus able to place the attachment portion 5 directly in their mouth and remove the aerosol 2 by breathing in from the inhalation device 1 or container 8, i.e. to suck out the aerosol 2.

In the embodiment shown, the inhalation device 1 is particularly preferably formed solely by the connecting device 4 and the container 8 and optionally the fixing means 10 (if required and if it does not form part of the connecting device 4 or container 8).

The connecting device 4 is preferably designed to be re-used numerous times and, in particular, is of very simple construction and easy to clean, particularly as it is dishwasher-safe, and may optionally be cleaned by boiling.

In the embodiment shown, the connecting device 4 is preferably formed in one piece, particularly as an injection-moulded component, with the attachment portion 5 and the connecting portion 9. The connecting device 4, however, may also be constructed in several parts or made up of a number of components which are releasable or non-releasable.

The connecting device 4 is preferably made of a suitable plastics.

The inhalation device 1 or the connecting device 4 preferably widens out from the attachment portion 5 to the container 8 or to the connecting portion 9, more particularly in a funnel shape. However, other design solutions are also possible.

The container 8 is preferably to be used only once or is designed as a disposable item, and may, for example, be a standard commercial bag or cone such as a sandwich bag or the like.

The inhalation device 1 or the connecting device 4 may optionally have a valve or control device 14 which is shown solely by dashed lines in FIG. 1. This valve or control device 14 may, for example, control or regulate the inflow and/or outflow resistance or the inflow and/or outflow rate and/or allow temporary closure.

A second embodiment of the proposed inhalation device 1 will be explained hereinafter with reference to FIGS. 2 to 4, the following description focusing on essential differences and/or additional aspects. The remarks and explanations given previously continue to apply in a supplementary or corresponding manner, in particular. Moreover, the two embodiments or individual aspects and features of the embodiments may also be combined with one another as desired but may also be implemented independently of one another and optionally in other different inhalation devices as well.

Figure 2:
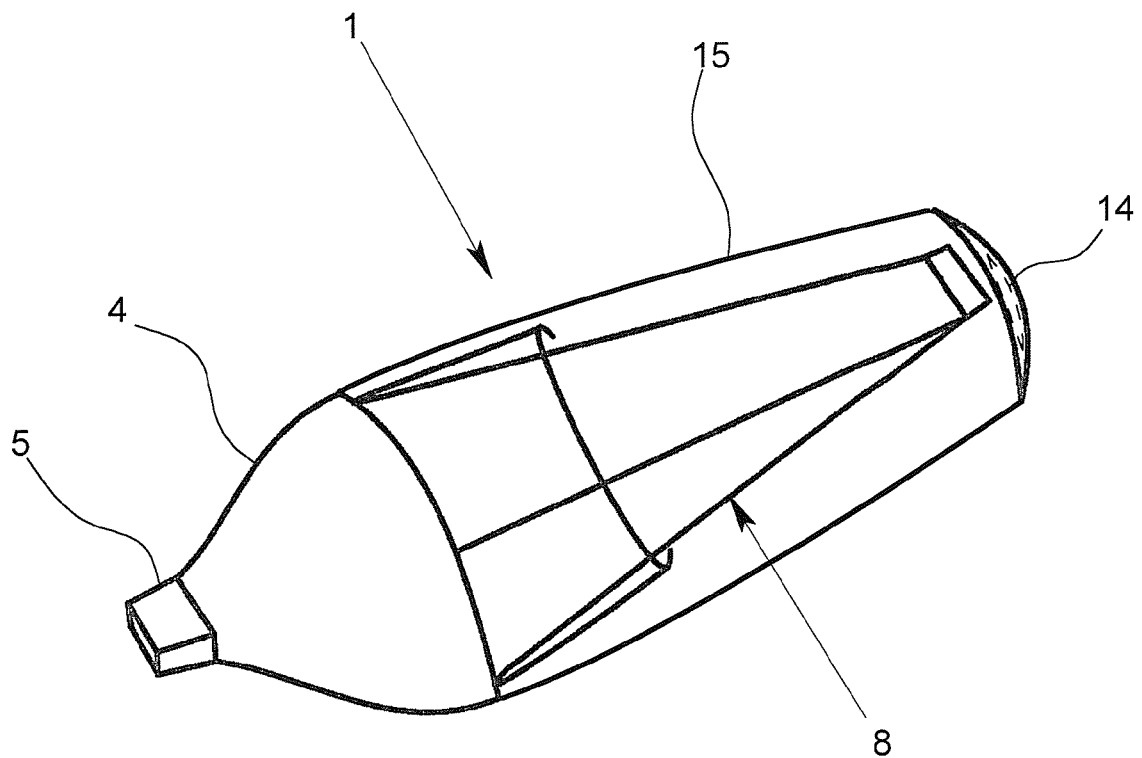
FIG. 2 shows a schematic view of a proposed inhalation device according to a second embodiment.

FIG. 2 is a schematic view of the inhalation device 1 according to the second embodiment. This embodiment preferably corresponds substantially to the embodiment of an inhalation device described in EP 1163921 B1 in FIG. 6a or b.

In contrast to the bellows-shaped container collapsing in the axial direction, the inhalation device 1 according to the second embodiment comprises the container 8 according to the first embodiment. The container 8 is thus preferably at least substantially wedge-shaped and/or configured such that it at least substantially maintains its length on collapsing. Moreover, the container 8 preferably tapers towards its free end 11.

The inhalation device 1 according to the second embodiment comprises, in contrast to the first embodiment, a housing 15, in particular, which surrounds the container 8. The housing 15 is preferably at least partly transparent or translucent so that the container 8 is visible, in particular to enable the user to see or check whether the container 8 has expanded, collapsed or to what extent it has collapsed.

The housing 15 is preferably releasably connected or connectable to the connecting device 4 at one end. At the other or free end the housing 15 preferably comprises the optional valve or control device 14.

In the second embodiment, the container 8 is preferably arranged in the inhalation device 1 or in the housing 15 such that when it expands to receive aerosol 2 into the container 8 and/or when it collapses for aerosol 2 to be removed from the container 8, air flows out of or into the space surrounding the container 8 from the inhalation device 1 or from the housing 15. This air current is preferably throttled and/or controlled or regulated, particularly preferably by the optional valve or control device 14. However, other design solutions are also possible.

The connecting portion 9 of the connecting device 4 for the container 8 is not visible in FIG. 2 but is covered, for example, by an external housing portion of the inhalation device 1 or the connecting device 4 or the housing 15.

Figure 3:
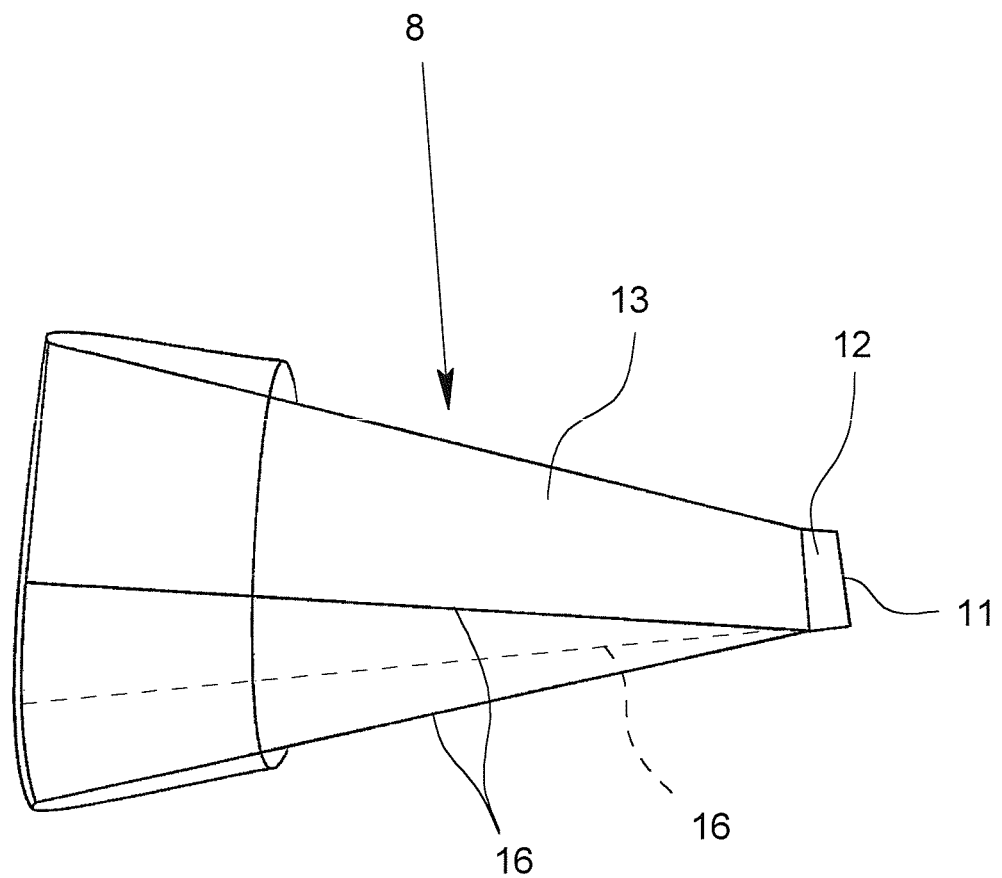
FIG. 3 shows a schematic view of a container of the inhalation device.

FIG. 3 is a perspective view of the container 8 which preferably comprises at least one flexing, folding or bending edge 16, particularly preferably on both sides and/or along both flat sides 13, which extends at least substantially in the longitudinal direction and/or in the main direction of inflow or outflow of the aerosol 2, in order to enable or ensure a defined and/or easy collapse of the container 8 when aerosol 2 is removed, i.e. on inhaling.

Figure 4:
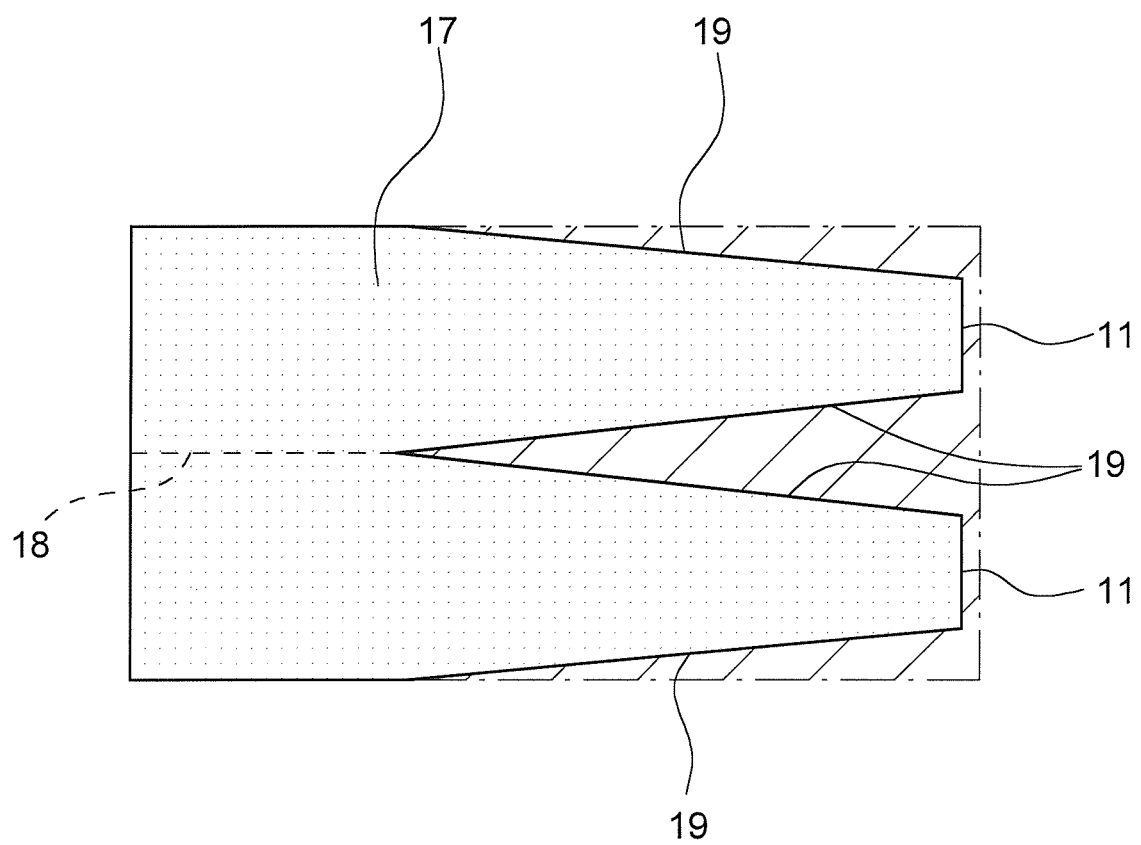
FIG. 4 shows a schematic cutting pattern for producing the container.

The container 8 is preferably made from a piece of material or blank 17, as indicated by way of example in FIG. 4. The blank 17 is formed, for example, by cutting a larger piece of material to size, in the embodiment shown by cutting away the broadly shaded areas.

The blank 17 is preferably folded lengthwise, in this case along the line 18, and/or in such a way that two pieces of material or areas come to lie on top of one another, which are then joined together at the longitudinal edges 19 and at the free end 11, particularly by gluing, sealing and/or welding.

Thus a collapsible bag is formed as the container 8. The bag 8 is of open design at the end opposite the free end 11 and at this end it is preferably releasably connectable to the inhalation device 1 or to the connecting device 4 or to the connecting portion 9.

Thus the container 8 can be produced in a very simple and inexpensive manner.

Experiments with a measuring device have shown that the fine particle count can be substantially increased by the proposed shaping or modification of the container 8. In particular, the fine particle count can be increased by more than 50%, starting from the known inhalation device shown in FIG. 6a of EP 1163921 B1, by modifying the container 8, as has been demonstrated in tests.

It should be noted that the inhalation device 1 or the container 8 preferably only holds a specific aerosol volume.

It should be noted that the container 8 is preferably not of self-expanding construction.

A particularly preferred embodiment of the inhaler 3 will be explained in more detail hereinafter.

Figure 5:
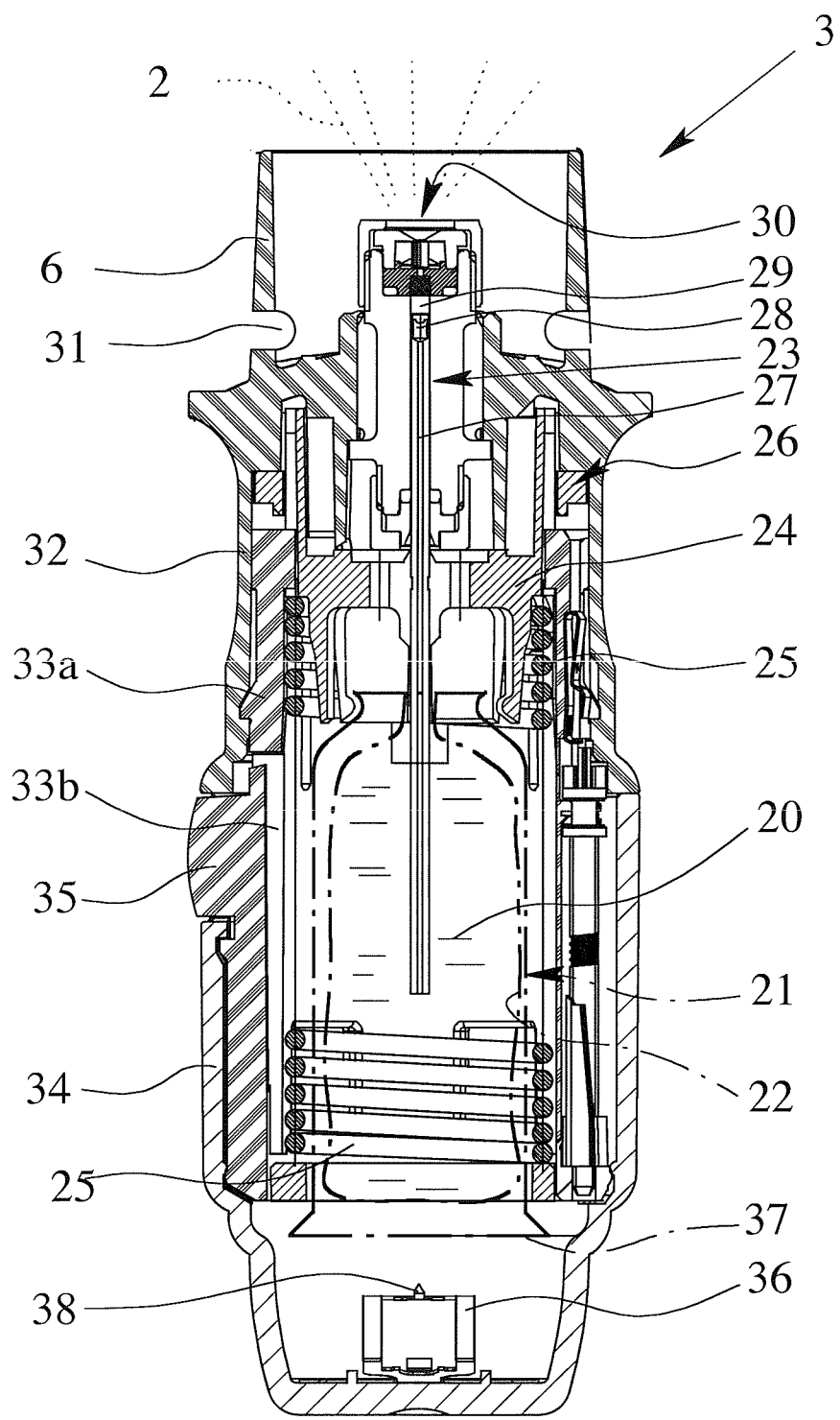
FIG. 5 shows a schematic section through the inhaler according to a preferred embodiment, in the untensioned state.
Figure 6:
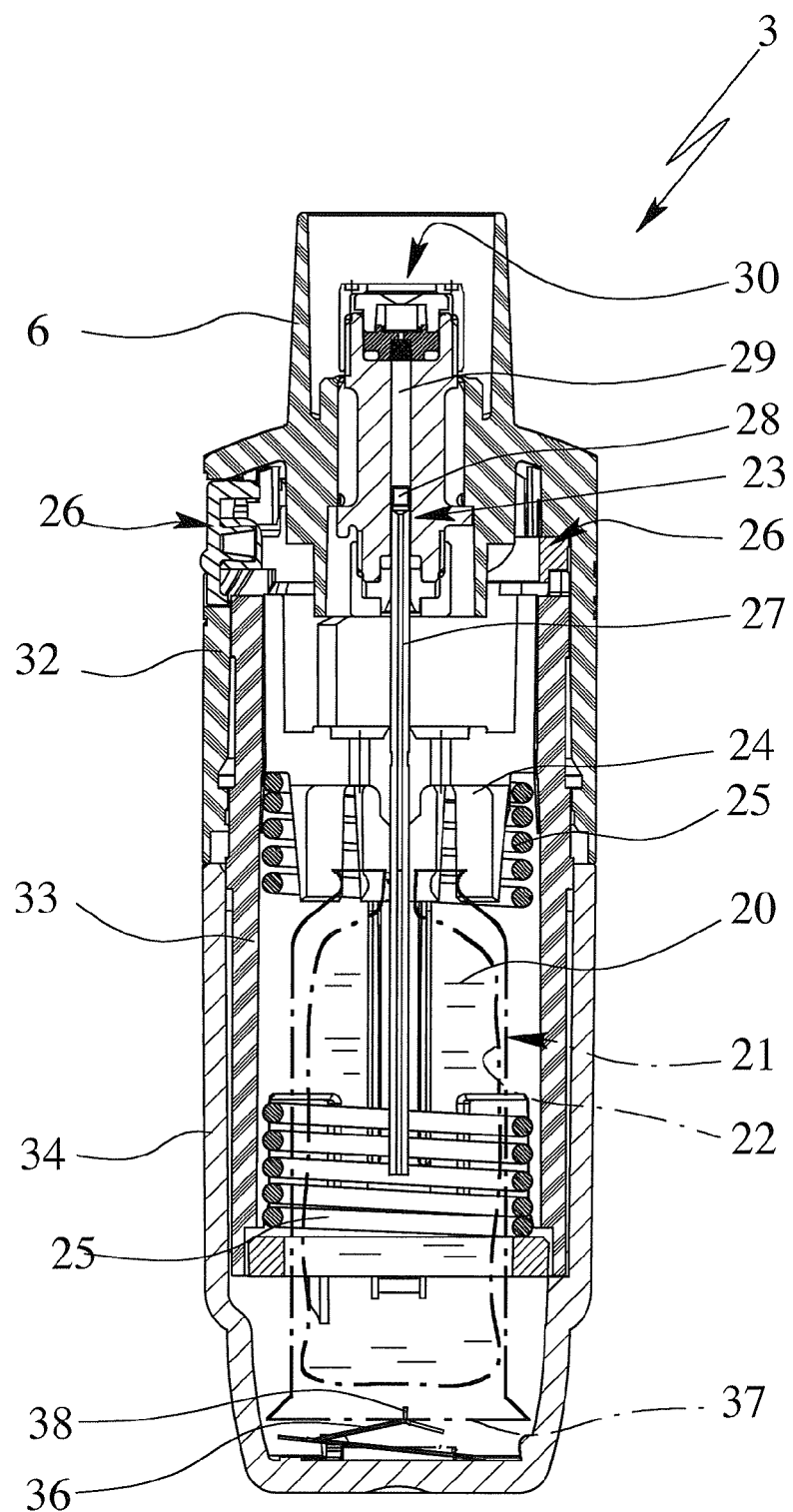
FIG. 6 shows a schematic section through the inhaler in the tensioned state, rotated through 90° compared with FIG. 5.

FIGS. 5 and 6 show a proposed portable inhaler 3 for the propellant-free nebulisation of a medicament preparation 20 in schematic view in the untensioned state (FIG. 5) and in the tensioned state (FIG. 6). FIGS. 5 and 6 show the inhaler 3 with a container 21 holding the medicament preparation 20.

During the nebulisation of the medicament preparation 20, preferably a fluid, a lung-bound aerosol 2 (FIG. 5) is formed which can be breathed in or inhaled by a user or patient (not shown). Usually inhalation takes place at least once a day, particularly several times a day, preferably at predetermined intervals, more particularly as a function of the patient's illness.

The inhaler 3 comprises the preferably insertable and optionally replaceable container 21 with the medicament preparation 20. The container 21 thus forms a reservoir for the medicament preparation 20 that is to be nebulised. Preferably, the container 21 contains a sufficient quantity of medicament preparation 20 or active substance for several doses of the medicament preparation 20, i.e. to permit several nebulisations or applications. A typical container 21 as disclosed in WO 96/06011 A1 holds a volume of about 2-10 ml. With regard to the preferred construction of the container 21 reference is additionally made to WO 00/49988 A2.

The container 21 is preferably substantially cylindrical or cartridge-shaped and after the inhaler 3 has been opened the container can be inserted therein from below and optionally replaced. It is preferably of rigid construction, the medicament preparation 20 being contained in particular in a collapsible bag 22 in the container 21.

The inhaler 3 also comprises a conveying device, particularly a pressure generator 23, for conveying and nebulising the medicament preparation 20, particularly in a predetermined and optionally adjustable dosage amount in each case.

The inhaler 3 or pressure generator 23 comprises in particular a holder 24 for the container 21, the associated drive spring 25, which is only partly shown, preferably having an associated locking element 26 which is manually operable to release it, a conveying element, preferably a conveying tube 27 in the form of a capillary, with an optional valve, particularly a non-return valve 28, a pressure chamber 29 and/or an expulsion nozzle 30, particularly in the region of a mouthpiece 6.

The container 21 is fixed in the inhaler 1 by means of the holder 24, particularly by a clamping or latching action, such that the conveying tube 27 protrudes into the container 21. The holder 24 may be constructed such that the container 21 can be exchanged.

For tensioning the drive spring 25 the holder 24 with the container 21 and the conveying tube 27 is moved downwards in the figures and the medicament preparation 20—or more precisely the next dose—is sucked out of the container 21 into the pressure chamber 29 of the pressure generator 23 through the non-return valve 28.

During the subsequent spring relaxation after operation of the locking element 26, the medicament preparation 20 in the pressure chamber 29 is placed under pressure by moving the conveying tube 27 back up, with the non-return valve 28 now closed, by releasing the tension on the tensioned drive spring 25b, so that this conveying tube 27 now acts as a pressure ram. This pressure expels the medicament preparation 20 through the expulsion nozzle 30, where it is nebulised into the preferably inhalable aerosol 2, as shown in FIG. 5.

The user or patient (not shown) can inhale the aerosol 2, while preferably supply air can be sucked into the mouthpiece 6 through at least one supply air opening 31.

During the nebulisation process the container 21 is moved back into its original position by the relaxation of tensioned drive spring 25b. The container 21 thus performs a lifting movement during the tensioning process and during the nebulisation process.

The inhaler 3 comprises in particular a first housing part (upper housing part) 32 and an inner part 33 which is rotatable relative thereto (FIG. 6) having an upper part 33a and a lower part 33b (FIG. 5), while a second housing part (lower housing part) 34, which is in particular manually operable or rotatable, is releasably attached, in particular pushed onto the inner part 17, preferably by means of a safety closure or retaining element 35. In particular, the safety closure or retaining element 35 is configured such that accidental opening of the inhaler 3 or removal of the second housing part 34 is prevented. In particular, in order to release the second housing part 34, the retaining element 35 has to be pressed in against spring force. In order to insert and/or replace the container 21, the second housing part 34 can be detached from the inhaler 1. The second housing part 34 preferably forms a cap-like lower housing part and/or engages around or over a lower free end portion of the container 21.

The second housing part 34 can be rotated relative to the first housing part 32, whereby the inner part 33 is also rotated. In this way the drive spring 25 is tensioned in the axial direction by means of a gear (not shown in detail) acting on the holder 24. During tensioning the container 21 is moved axially downwards or with its end portion (further) into the second housing part 34 or towards the end face thereof, until the container 21 assumes an end position shown in FIG. 6. In this state the drive spring 25 or the inhaler 3 is clamped and locked with locking element 26 (shown in two views in FIG. 6).

The inhaler 3 preferably has a device for forcibly ventilating the container 21.

When tensioning first takes place, the container 21 is preferably pierced in its base or opened. In particular, an axially acting spring 36 arranged in the housing part 34 comes to abut on the container base 37 and with a piercing element 38 pierces the container 21 or an in particular gastight seal provided in the base for ventilation purposes when contact is first made.

The device for forcible ventilation is thus formed in this case by the piercing element 38, which is held or formed by the spring 36. However, other design solutions are also possible.

It should be noted that during the piercing for ventilation purposes, only the outer shell of the container 21 is opened. The bag 22 containing the medicament preparation 20 remains undamaged. As the medicament formulation 20 is removed from the bag 22 through the conveying tube 27 the flexible bag 22 collapses. For pressure equalisation, ambient air can flow into the container 21 through the ventilation or piercing opening.

In order to use the inhaler 3, first of all the container 21 has to be inserted. This is preferably done by removing or pulling out the second housing part 34. The container 21 is then axially inserted or pushed into the inner part 33. At the same time the container 21 is opened at the head end or attached. This is done by means of the conveying element, i.e. the conveying tube 27, which pierces a seal preferably provided at the head end of the container 21 and is then inserted through a septum at the head end of the container 21 into the interior of the bag 22. Thus the fluidic connection is made between the container 21, or more accurately between the bag 22 in the container 21, via the conveying tube 27 to the pressure generator 23 or pressure chamber 29.

Then the second housing part 34 is pushed on again. The inhaler 3 can now be tensioned for the first time. At this stage the container 21 is then pierced at its base by the piercing element 38, i.e. forcibly ventilated, as explained previously.

After the container 21 has been inserted and fluidically connected and before it is used for the first time, the inhaler 3 is preferably tensioned and triggered several times. This so-called priming displaces any air present in the medicament preparation 20 in the conveying tube 27 and in the pressure generator 23 to the expulsion nozzle 30. The inhaler 3 is then ready for inhalation.

The quantity of medicament preparation 20 delivered per spray or nebulisation process is preferably about 10 µl to 50 µl, more particularly about 10 µl to 20 µl, most preferably about 15 µl.

The drive spring 25 is preferably installed in a biased state in order to achieve a high spring pressure. In fact, in the proposed inhaler 3 the pressurisation and conveying of the medicament preparation 20 during the nebulisation process takes place preferably only by spring force, and more particularly only by the force of the drive spring 25.

The inhaler 3 is preferably configured such that the medicament preparation 20 in the pressure generator 23 or in the pressure chamber 29 reaches a pressure of 5 MPa to 60 MPa, particularly about 10 MPa to 50 MPa during delivery. Particularly preferably, during the delivery or nebulisation of the medicament preparation 20, a pressure of about 5 MPa to 60 MPa, more particularly about 10 to 30 MPa, is reached at the expulsion nozzle 30 or at the nozzle openings thereof. The medicament preparation 20 is then converted into the aerosol 2, the droplets of which have an aerodynamic diameter of up to 20 µm, preferably about 3 µm to 10 µm. The nebulising activity or nebulising effect is achieved or further assisted by preferably intercepting jets delivered by the expulsion nozzle 30.

The inhaler 3 is preferably constructed such that the aerosol 2 is delivered at low speed, particularly at a speed of less than 2 m/s, most preferably about 1.6 m/s or less (in each case measured at a distance of 10 cm from the expulsion nozzle 30). The inhaler 3 is thus preferably in the form of a so-called SMI (soft mist inhaler). The low dispensing speed can be obtained or assisted by intercepting jets of the medicament preparation 20, which are delivered by the expulsion nozzle 30 and/or by a suitable choice of spring force.

Particularly preferably, the construction of the inhaler 3 is such that the aerosol generation lasts for at least 1 s, in particular for at least 1.5 s. The time taken to nebulise a dose or to actuate the inhaler 1 is thus at least 1 s, more particularly more than 1.5 s.

To complete the disclosure of the present application and with regard to the preferred embodiment of the inhaler 3, reference is hereby made, by way of a precaution, to the total disclosure of both WO 91/14468 A1 and also WO 97/12687 A1.

In contrast to freestanding appliances or the like, the proposed inhaler 3 is preferably designed to be portable and in particular is a mobile hand-held device.

By virtue of its cylindrical shape and handy size of less than 9 to 15 cm long and 2 to 4 cm wide, the inhaler 3 can be carried by the patient at all times. The nebuliser sprays a defined volume of the medicament preparation 20 by the application of high pressure through small nozzles, so as to form inhalable aerosols 2.

The proposed inhaler 3 operates purely mechanically, in particular. However, the inhaler 3 may theoretically operate by any other method. In particular, the expression "conveying device" or "pressure generator" must be understood in very general terms. For example, the pressure required for the delivery and nebulisation may also be produced by propellant gas, a pump or any other suitable method.

The proposed inhaler 3 is designed in particular for the brief nebulisation of the medicament preparation 20, for example for one to two breaths. However, it may also be designed or used for longer or continuous nebulisation.

Some preferred compounds, ingredients and/or formulations of the medicament preparation 20 are listed below.

The compounds listed below may be used in the device according to the invention on their own or in combination. In the compounds mentioned below, W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the device according to the invention. Combinations of W might be, for example:

W denotes a betamimetic, combined with an anticholinergic, corticosteroid, PDE4-inhibitor, EGFR-inhibitor or LTD4-antagonist, W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide 5-[2-(5,6-diethyl-indan-2-ylamino)-1-hydroxy-ethyl]-8-hydroxy-1H-quinolin-2-one 4-hydroxy-7-[2-{[2-{[3-(2-phenylethoxy)propyl]sulphonyl}ethyl]amino}ethyl]-2(3H)-benzothiazolone 1-(2-fluoro-4-hydroxyphenyl)-2-[4-(1-benzimidazolyl)-2-methyl-2-butylamino]ethanol
1-[3-(4-methoxybenzyl-amino)-4-hydroxyphenyl]-2-[4-(1-benzimidazolyl)-2-methyl-2-butylamino]ethanol
1-[2H-5-hydroxy-3-oxo-4H-1,4-benzoxazin-8-yl]-2-[3-(4-N,N-dimethylaminophenyl)-2-methyl-2-propylamino]ethanol
1-[2H-5-hydroxy-3-oxo-4H-1,4-benzoxazin-8-yl]-2-[3-(4-methoxyphenyl)-2-methyl-2-propylamino]ethanol
1-[2H-5-hydroxy-3-oxo-4H-1,4-benzoxazin-8-yl]-2-[3-(4-n-butyloxyphenyl)-2-methyl-2-propylamino]ethanol
1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol
5-hydroxy-8-(1-hydroxy-2-isopropylaminobutyl)-2H-1,4-benzoxazin-3-(4H)-one
1-(4-amino-3-chloro-5-trifluoromethylphenyl)-2-tert.-butylamino)ethanol
6-hydroxy-8-{1-hydroxy-2-[2-(4-methoxy-phenyl)-1,1-dimethyl-ethylamino]-ethyl}-4H-benzo[1,4]oxazin-3-one
6-hydroxy-8-{1-hydroxy-2-[2-(ethyl 4-phenoxy-acetate)-1,1-dimethyl-ethylamino]-ethyl}-4H-benzo[1,4]oxazin-3-one
6-hydroxy-8-{1-hydroxy-2-[2-(4-phenoxy-acetic acid)-1,1-dimethyl-ethylamino]-ethyl}-4H-benzo[1,4]oxazin-3-one
8-{2-[1,1-dimethyl-2-(2,4,6-trimethylphenyl)-ethylamino]-1-hydroxy-ethyl}-6-hydroxy-4H-benzo[1,4]oxazin-3-one
6-hydroxy-8-{1-hydroxy-2-[2-(4-hydroxy-phenyl)-1,1-dimethyl-ethylamino]-ethyl}-4H-benzo[1,4]oxazin-3-one
6-hydroxy-8-{1-hydroxy-2-[2-(4-isopropyl-phenyl)-1,1-dimethyl-ethylamino]-ethyl}-4H-benzo[1,4]oxazin-3-one
8-{2-[2-(4-ethyl-phenyl)-1,1-dimethyl-ethylamino]-1-hydroxy-ethyl}-6-hydroxy-4H-benzo[1,4]oxazin-3-one
8-{2-[2-(4-ethoxy-phenyl)-1,1-dimethyl-ethylamino]-1-hydroxy-ethyl}-6-hydroxy-4H-benzo[1,4]oxazin-3-one
4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid
8-{2-[2-(3,4-difluoro-phenyl)-1,1-dimethyl-ethylamino]-1-hydroxy-ethyl}-6-hydroxy-4H-benzo[1,4]oxazin-3-one
1-(4-ethoxy-carbonylamino-3-cyano-5-fluorophenyl)-2-(tert-butylamino)ethanol
2-hydroxy-5-(1-hydroxy-2-{2-[4-(2-hydroxy-2-phenyl-ethylamino)-phenyl]-ethylamino}-ethyl)-benzaldehyde
N-[2-hydroxy-5-(1-hydroxy-2-{2-[4-(2-hydroxy-2-phenyl-ethylamino)-phenyl]-ethylamino}-ethyl)-phenyl]-formamide
8-hydroxy-5-(1-hydroxy-2-{2-[4-(6-methoxy-biphenyl-3-ylamino)-phenyl]-ethylamino}-ethyl)-1H-quinolin-2-one
8-hydroxy-5-[1-hydroxy-2-(6-phenethylamino-hexylamino)-ethyl]-1H-quinolin-2-one
5-[2-(2-{4-[4-(2-amino-2-methyl-propoxy)-phenylamino]-phenyl}-ethylamino)-1-hydroxy-ethyl]-8-hydroxy-1H-quinolin-2-one
[3-(4-{6-[2-hydroxy-2-(4-hydroxy-3-hydroxymethyl-phenyl)-ethylamino]-hexyloxy}-butyl)-5-methyl-phenyl]-urea
4-(2-{6-[2-(2,6-dichloro-benzyloxy)-ethoxy]-hexylamino}-1-hydroxy-ethyl)-2-hydroxymethyl-phenol
3-(4-{6-[2-hydroxy-2-(4-hydroxy-3-hydroxymethyl-phenyl)-ethylamino]-hexyloxy}-butyl)-benzylsulphonamide
3-(3-{7-[2-hydroxy-2-(4-hydroxy-3-hydroxymethyl-phenyl)-ethylamino]-heptyloxy}-propyl)-benzylsulphonamide
4-(2-{6-[4-(3-cyclopentanesulphonyl-phenyl)-butoxy]-hexylamino}-1-hydroxy-ethyl)-2-hydroxymethyl-phenol
N-Adamantan-2-yl-2-(3-{2-[2-hydroxy-2-(4-hydroxy-3-hydroxymethyl-phenyl)-ethylamino]-propyl}-phenyl)-acetamide optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

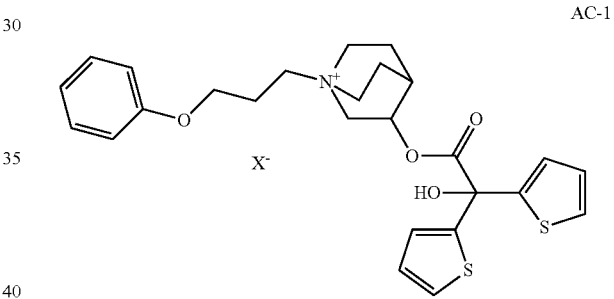

AC-1 wherein $X^-$ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-en

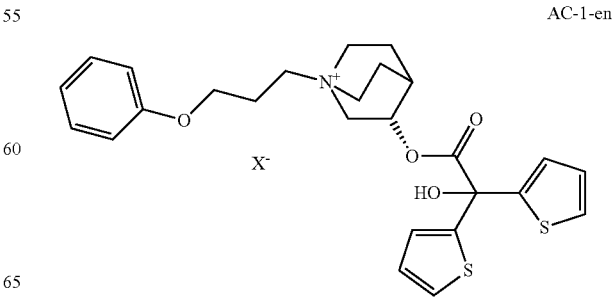

AC-1-en wherein X⁻ may have the above-mentioned meanings. Other preferred anticholinergics are selected from the salts of formula AC-2

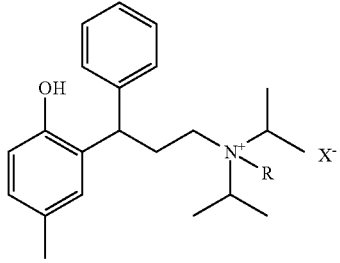

AC-2 wherein R denotes either methyl or ethyl and wherein X⁻ may have the above-mentioned meanings. In an alternative embodiment the compound of formula AC-2 may also be present in the form of the free base AC-2-base.

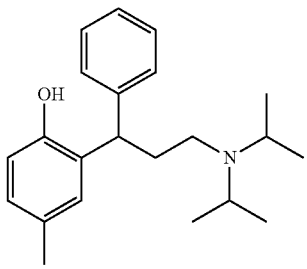

AC-2-base

Other specified compounds are:
tropenol 2,2-diphenylpropionate methobromide;
scopine 2,2-diphenylpropionate methobromide;
scopine 2-fluoro-2,2-diphenylacetate methobromide;
tropenol 2-fluoro-2,2-diphenylacetate methobromide;
tropenol 3,3',4,4'-tetrafluorobenzilate methobromide;
scopine 3,3',4,4'-tetrafluorobenzilate methobromide;
tropenol 4,4'-difluorobenzilate methobromide;
scopine 4,4'-difluorobenzilate methobromide;
tropenol 3,3'-difluorobenzilate methobromide;
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate methobromide;
scopine 9-methyl-xanthene-9-carboxylate methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, The above-mentioned compounds may also be used as salts within the scope of the present invention, wherein instead of the methobromide the metho-X salts are used, wherein X may have the meanings given hereinbefore for X⁻.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and
(S)-fluoromethyl 6,9-difluoro-17-[(2-furanylcarbonyl)oxy]-11-hydroxy-16-methyl-3-oxo-androsta-1,4-diene-17-carbothionate
(S)-(2-oxo-tetrahydro-furan-3S-yl)6,9-difluoro-11-hydroxy-16-methyl-3-oxo-17-propionyloxy-androsta-1,4-diene-17-carbothionate,
cyanomethyl 6α,9α-difluoro-11β-hydroxy-16α-methyl-3-oxo-17α-(2,2,3,3-tertamethylcyclopropylcarbonyl)oxy-androsta-1,4-diene-17β-carboxylate
optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, CI-1018, CDC-801, CDC-3052, D-22888, YM-58997, Z-15370 and
N-(3,5-dichloro-1-oxo-pyridin-4-yl)-4-difluoromethoxy-3-cyclopropylmethoxybenzamide
(−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide
(R)-(+)-1-(4-bromobenzyl)-4-[(3-cyclopentyloxy)-4-methoxyphenyl]-2-pyrrolidone
3-(cyclopentyloxy-4-methoxyphenyl)-1-(4-N'-[N-2-cyano-S-methyl-isothioureido]benzyl)-2-pyrrolidone
cis[4-cyano-4-(3-cyclopentyloxy-4-methoxyphenyl)cyclohexane-1-carboxylic acid]
2-carbomethoxy-4-cyano-4-(3-cyclopropylmethoxy-4-difluoromethoxyphenyl)cyclohexan-1-one
cis[4-cyano-4-(3-cyclopropylmethoxy-4-difluoromethoxyphenyl)cyclohexan-1-ol]
(R)-(+)-ethyl[4-(3-cyclopentyloxy-4-methoxyphenyl)pyrrolidin-2-ylidene]acetate
(S)-(−)-ethyl[4-(3-cyclopentyloxy-4-methoxyphenyl)pyrrolidin-2-ylidene]acetate
9-cyclopentyl-5,6-dihydro-7-ethyl-3-(2-thienyl)-9H-pyrazolo[3,4-c]-1,2,4-triazolo[4,3-a]pyridine
9-cyclopentyl-5,6-dihydro-7-ethyl-3-(tert-butyl)-9H-pyrazolo[3,4-c]-1,2,4-triazolo[4,3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid

[2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyhamino]-6-{[4-(morpholin-4-yl)-1-oxo-2-buten-1-yl]amino}-7-cyclopropylmethoxy-quinazoline 4-[(3-chloro-4-fluorophenyhamino]-6-{[4-(N,N-diethylamino)-1-oxo-2-buten-1-yl]-amino}-7-cyclopropylmethoxy-quinazoline 4-[(3-chloro-4-fluorophenyhamino]-6-{[4-(N,N-dimethylamino)-1-oxo-2-buten-1-yl]amino}-7-cyclopropylmethoxy-quinazoline 4-[(R)-(1-phenyl-ethyl)amino]-6-{[4-(morpholin-4-yl)-1-oxo-2-buten-1-yl]amino}-7-cyclopentyloxy-quinazoline 4-[(3-chloro-4-fluoro-phenyhamino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyhamino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyhamino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxyethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-to-(2-methoxyethyl)-amino)-1-oxo-2-buten-1-yl]amino}-7-cyclopropylmethoxy-quinazoline 4-[(R)-(1-phenyl-ethyl)amino]-6-({4-[N-(2-methoxyethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxyethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxyethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6,7-to-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline 4-[(3-chloro-4-fluorophenyl)amino]-6-({4-[N,N-to-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5.5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxy-carbonyl)-piperidin-4-yloxy]-7-methoxy-quinazoline
4-[(3-chloro-4-fluoro-phenyl)amino]-6-(trans-4-amino-cyclohexan-1-yloxy)-7-methoxy-quinazoline
4-[(3-chloro-4-fluoro-phenyl)amino]-6-(trans-4-methanesulphonylamino-cyclohexan-1-yloxy)-7-methoxy-quinazoline
4-[(3-chloro-4-fluoro-phenyl)amino]-6-(tetrahydropyran-3-yloxy)-7-methoxy-quinazoline
4-[(3-chloro-4-fluoro-phenyl)amino]-6-(1-methyl-piperidin-4-yloxy)-7-methoxy-quinazoline
4-[(3-chloro-4-fluoro-phenyl)amino]-6-{1-[(morpholin-4-yl)carbonyl]-piperidin-4-yloxy}-7-methoxy-quinazoline
4-[(3-chloro-4-fluoro-phenyl)amino]-6-{1-[(methoxymethyl)carbonyl]-piperidin-4-yloxy}-7-methoxy-quinazoline
4-[(3-chloro-4-fluoro-phenyl)amino]-6-(piperidin-3-yloxy)-7-methoxy-quinazoline
4-[(3-chloro-4-fluoro-phenyl)amino]-6-[1-(2-acetylamino-ethyl)-piperidin-4-yloxy]-7-methoxy-quinazoline
4-[(3-chloro-4-fluoro-phenyl)amino]-6-(tetrahydropyran-4-yloxy)-7-ethoxy-quinazoline
4-[(3-chloro-4-fluoro-phenyl)amino]-6-((S)-tetrahydrofuran-3-yloxy)-7-hydroxy-quinazoline
4-[(3-chloro-4-fluoro-phenyl)amino]-6-(tetrahydropyran-4-yloxy)-7-(2-methoxy-ethoxy)-quinazoline
4-[(3-chloro-4-fluoro-phenyl)amino]-6-{trans-4-[(dimethylamino)sulphonylamino]-cyclohexan-1-yloxy}-7-methoxy-quinazoline
4-[(3-chloro-4-fluoro-phenyl)amino]-6-{trans-4-[(morpholin-4-yl)carbonylamino]-cyclohexan-1-yloxy}-7-methoxy-quinazoline
4-[(3-chloro-4-fluoro-phenyl)amino]-6-{trans-4-[(morpholin-4-yl)sulphonylamino]-cyclohexan-1-yloxy}-7-methoxy-quinazoline
4-[(3-chloro-4-fluoro-phenyl)amino]-6-(tetrahydropyran-4-yloxy)-7-(2-acetylamino-ethoxy)-quinazoline
4-[(3-chloro-4-fluoro-phenyl)amino]-6-(tetrahydropyran-4-yloxy)-7-(2-methanesulphonylamino-ethoxy)-quinazoline
4-[(3-chloro-4-fluoro-phenyl)amino]-6-{1-[(piperidin-1-yl)carbonyl]-piperidin-4-yloxy}-7-methoxy-quinazoline
4-[(3-chloro-4-fluoro-phenyl)amino]-6-(1-aminocarbonylmethyl-piperidin-4-yloxy)-7-methoxy-quinazoline
4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline
4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline
4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline
4-[(3-chloro-4-fluoro-phenyl)amino]-6-(trans-4-ethanesulphonylamino-cyclohexan-1-yloxy)-7-methoxy-quinazoline
4-[(3-chloro-4-fluoro-phenyl)amino]-6-(1-methanesulphonyl-piperidin-4-yloxy)-7-ethoxy-quinazoline
4-[(3-chloro-4-fluoro-phenyl)amino]-6-(1-methanesulphonyl-piperidin-4-yloxy)-7-(2-methoxy-ethoxy)-quinazoline
4-[(3-chloro-4-fluoro-phenyl)amino]-6-[1-(2-methoxy-acetyl)-piperidin-4-yloxy]-7-(2-methoxy-ethoxy)-quinazoline
4-[(3-chloro-4-fluoro-phenyl)amino]-6-(cis-4-acetylamino-cyclohexan-1-yloxy)-7-methoxy-quinazoline
4-[(3-ethynyl-phenyl)amino]-6-[1-(tert.-butyloxycarbonyl)-piperidin-4-yloxy]-7-methoxy-quinazoline
4-[(3-ethynyl-phenyl)amino]-6-(tetrahydropyran-4-yloxy)-7-methoxy-quinazoline
4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline
4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline
4-[(3-chloro-4-fluoro-phenyl)amino]-6-{cis-4-[(morpholin-4-yl)carbonylamino]-cyclohexan-1-yloxy}-7-methoxy-quinazoline
4-[(3-chloro-4-fluoro-phenyl)amino]-6-{1-[2-(2-oxopyrrolidin-1-yl)ethyl]-piperidin-4-yloxy}-7-methoxy-quinazoline
4-[(3-chloro-4-fluoro-phenyl)amino]-6-{1-[(morpholin-4-yl)carbonyl]-piperidin-4-yloxy}-7-(2-methoxy-ethoxy)-quinazoline
4-[(3-ethynyl-phenyl)amino]-6-(1-acetyl-piperidin-4-yloxy)-7-methoxy-quinazoline
4-[(3-ethynyl-phenyl)amino]-6-(1-methyl-piperidin-4-yloxy)-7-methoxy-quinazoline
4-[(3-ethynyl-phenyl)amino]-6-(1-methanesulphonyl-piperidin-4-yloxy)-7-methoxy-quinazoline
4-[(3-chloro-4-fluoro-phenyl)amino]-6-(1-methyl-piperidin-4-yloxy)-7(2-methoxy-ethoxy)-quinazoline
4-[(3-chloro-4-fluoro-phenyl)amino]-6-(1-isopropyloxycarbonyl-piperidin-4-yloxy)-7-methoxy-quinazoline
4-[(3-chloro-4-fluoro-phenyl)amino]-6-(cis-4-methylamino-cyclohexan-1-yloxy)-7-methoxy-quinazoline
4-[(3-chloro-4-fluoro-phenyl)amino]-6-{cis-4-[N-(2-methoxy-acetyl)-N-methyl-amino]-cyclohexan-1-yloxy}-7-methoxy-quinazoline
4-[(3-ethynyl-phenyl)amino]-6-(piperidin-4-yloxy)-7-methoxy-quinazoline
4-[(3-ethynyl-phenyl)amino]-6-[1-(2-methoxy-acetyl)-piperidin-4-yloxy]-7-methoxy-quinazoline
4-[(3-ethynyl-phenyl)amino]-6-{1-[(morpholin-4-yl)carbonyl]-piperidin-4-yloxy}-7-methoxy-quinazoline
4-[(3-chloro-4-fluoro-phenyl)amino]-6-{1-[(cis-2,6-dimethyl-morpholin-4-yl)carbonyl]-piperidin-4-yloxy}-7-methoxy-quinazoline
4-[(3-chloro-4-fluoro-phenyl)amino]-6-{1-[(2-methyl-morpholin-4-yl)carbonyl]-piperidin-4-yloxy}-7-methoxy-quinazoline
4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline
4-[(3-chloro-4-fluoro-phenyl)amino]-6-{1-[(N-methyl-N-2-methoxyethyl-amino)carbonyl]-piperidin-4-yloxy}-7-methoxy-quinazoline
4-[(3-chloro-4-fluoro-phenyl)amino]-6-(1-ethyl-piperidin-4-yloxy)-7-methoxy-quinazoline
4-[(3-chloro-4-fluoro-phenyl)amino]-6-{1-[(2-methoxy-ethyl)carbonyl]-piperidin-4-yloxy}-7-methoxy-quinazoline
4-[(3-chloro-4-fluoro-phenyl)amino]-6-{1-[(3-methoxypropyl-amino)-carbonyl]-piperidin-4-yloxy}-7-methoxy-quinazoline
4-[(3-chloro-4-fluoro-phenyl)amino]-6-[cis-4-(N-methanesulphonyl-N-methyl-amino)-cyclohexan-1-yloxy]-7-methoxy-quinazoline
4-[(3-chloro-4-fluoro-phenyl)amino]-6-[cis-4-(N-acetyl-N-methyl-amino)-cyclohexan-1-yloxy]-7-methoxy-quinazoline 4-[(3-chloro-4-fluoro-phenyl)amino]-6-(trans-4-methylamino-cyclohexan-1-yloxy)-7-methoxy-quinazoline
4-[(3-chloro-4-fluoro-phenyl)amino]-6-[trans-4-(N-methanesulphonyl-N-methyl-amino)-cyclohexan-1-yloxy]-7-methoxy-quinazoline
4-[(3-chloro-4-fluoro-phenyl)amino]-6-(trans-4-dimethylamino-cyclohexan-1-yloxy)-7-methoxy-quinazoline
4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline
4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline
4-[(3-chloro-4-fluoro-phenyl)amino]-6-(1-methanesulphonyl-piperidin-4-yloxy)-7-methoxy-quinazoline
4-[(3-chloro-4-fluoro-phenyl)amino]-6-(1-cyano-piperidin-4-yloxy)-7-methoxy-quinazoline
optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorophenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

In addition, inhalable macromolecules as disclosed in EP 1 003 478 A1 or CA 2297174 A1 may also be used.

In addition, the compound may be selected from among the ergot alkaloid derivatives, the triptans, the CGRP-inhibitors, the phosphodiesterase-V inhibitors, optionally in the form of the racemates, enantiomers or diastereomers thereof, optionally in the form of the pharmacologically acceptable acid addition salts, the solvates and/or hydrates thereof.

Examples of ergot alkaloid derivatives are dihydroergotamine and ergotamine.

| List of reference numerals | |
|---|---|
| 1 | Inhalation device |
| 2 | aerosol |
| 3 | inhaler |
| 4 | connecting device |
| 5 | connecting portion |
| 6 | mouthpiece |
| 7 | receiving chamber |
| 8 | container |
| 9 | connecting portion |
| 10 | attachment means |
| 11 | free end |
| 12 | connecting seam |
| 13 | flat sides |
| 14 | valve or control device |
| 15 | housing |
| 16 | edge |
| 17 | blank |
| 18 | line |
| 19 | longitudinal edge |
| 20 | medicament preparation |
| 21 | container |
| 22 | bag |
| 23 | pressure generator |
| 24 | holder |
| 25 | drive spring |
| 26 | locking element |
| 27 | conveying tube |
| 28 | non-return valve |
| 29 | pressure chamber |
| 30 | expulsion nozzle |
| 31 | supply air opening |
| 32 | first housing part (upper housing part) |
| 33 | inner part |
| 33a | upper part of the inner part |
| 33b | lower part of the inner part |
| 34 | second housing part (lower housing part) |
| 35 | retaining element |
| 36 | spring (in lower housing part) |
| 37 | container base |
| 38 | piercing element |

The invention claimed is:

1. An inhalation device (1) for the intermediate storage of an aerosol (2), having a connecting device (4) and a container (8) for intermediately storing the aerosol (2) wherein the container (8) is connected or connectable to the connecting device (4) and collapses during inhalation, wherein
    the container (8) is configured so that as it collapses it maintains its length at least substantially, and
    the container (8) is folded longitudinally or foldable longitudinally for collapsing, and
    the container (8) is wedge-shaped in construction, and
    the cross-section of the container (8) is at its greatest in the region of the attachment to the connecting device (4) and the cross-section of the container (8) decreases continuously towards a free end (11) of the container (8), and further wherein the connecting device (4) has an attachment portion (5) for receiving and dispensing the fluid.

2. The inhalation device according to claim 1, characterized in that the container (8) has a flat free end (11).

3. The inhalation device according to claim 1, characterized in that the container (8) is made from a blank (17).

4. The inhalation device according to claim 1, characterized in that the container (8) consists of or is made from a flexible and/or soft material.

5. The inhalation device according to claim 1, characterized in that the container (8) is replaceable.

6. The inhalation device according to claim 1, characterized in that the container (8) is connected or connectable to the connecting device (4) by a clamping action.

7. The inhalation device according to claim 1, characterized in that the container (8) is releasably and/or replaceably connected or connectable to the connecting device (4).

8. The inhalation device according to claim 1, characterized in that the connecting device (4) has a connecting portion (9) and that the container (8) connected to the connecting device (4) through an elastic attachment (10) for holding the container (8) in a clamping and/or positively locking manner on the connecting portion (9) or an outer periphery of the connecting portion (9).

9. The inhalation device according to claim 1, characterized in that the connecting device has a tube-like connecting portion (9) for mounting the container (8).

10. The inhalation device according to claim 1, characterized in that the connecting device (4) comprises or forms an attachment portion (5).

11. The inhalation device according to claim 1, characterized in that the inhalation device (1) comprises a rigid housing (15) for the container (8).

12. The inhalation device according to claim 1, characterized in that the container (8) consists of or is made from film or paper.

13. The inhalation device according to claim 1, characterized in that the connecting device (4) has a connecting portion (9) and that the container (8) can be connected to the connecting device (4) by an annular attachment (10) for holding the container (8) in a clamping and/or positively locking manner on the connecting portion (9) or an outer periphery of the connecting portion (9).

14. The inhalation device according to claim 13, characterized in that the attachment (10) is an O-ring or clamping ring.

15. The inhalation device according to claim 1, characterized in that the free end (11) the container (8) is closed off.

16. The inhalation device according to claim 1, characterized in that the attachment portion (5) is tube-like.

17. The inhalation device according to claim 1, characterized in that the attachment portion (5) can be pushed onto or inserted into a mouthpiece (6) of an inhaler (3).

\* \* \* \* \*